United States Patent
Yamaguchi et al.

(10) Patent No.: US 11,717,150 B2
(45) Date of Patent: Aug. 8, 2023

(54) OPHTHALMOLOGIC APPARATUS, AND OPHTHALMOLOGIC INFORMATION PROCESSING APPARATUS

(71) Applicant: TOPCON CORPORATION, Tokyo (JP)

(72) Inventors: Tatsuo Yamaguchi, Warabi (JP); Ryoichi Hirose, Itabashi-ku (JP); Michiko Nakanishi, Katsushika-ku (JP)

(73) Assignee: TOPCON CORPORATION, Tokyo (JP)

( * ) Notice: Subject to any disclaimer, the term of this patent is extended or adjusted under 35 U.S.C. 154(b) by 297 days.

(21) Appl. No.: 16/885,305

(22) Filed: May 28, 2020

(65) Prior Publication Data

US 2020/0288966 A1 Sep. 17, 2020

Related U.S. Application Data

(63) Continuation of application No. PCT/JP2019/009004, filed on Mar. 7, 2019.

(30) Foreign Application Priority Data

Mar. 16, 2018 (JP) ................................. 2018-049744

(51) Int. Cl.
  *A61B 3/00* (2006.01)
  *A61B 3/10* (2006.01)
  *A61B 3/12* (2006.01)
(52) U.S. Cl.
  CPC ............ *A61B 3/0025* (2013.01); *A61B 3/102* (2013.01); *A61B 3/1005* (2013.01); *A61B 3/1225* (2013.01)
(58) Field of Classification Search
  None
  See application file for complete search history.

(56) References Cited

U.S. PATENT DOCUMENTS

2003/0103212 A1 6/2003 Westphal et al.
2008/0239240 A1* 10/2008 Tsukada ................ A61B 3/102
                                                            351/211

(Continued)

FOREIGN PATENT DOCUMENTS

CN          104146681 A    11/2014
JP         2011-224264 A   11/2011

(Continued)

OTHER PUBLICATIONS

Office Action dated Aug. 9, 2022, in corresponding Japanese patent Application No. 2018-049744, 11 pages.

(Continued)

*Primary Examiner* — Kyle Zhai
(74) *Attorney, Agent, or Firm* — Xsensus LLP

(57) ABSTRACT

An ophthalmologic apparatus includes an optical scanner, an interference optical system, an intraocular distance calculator, an image correcting unit, and a controller. The optical scanner is disposed at an optically substantially conjugate position with a first site of a subject's eye. The interference optical system is configured to split light from a light source into reference light and measurement light, to project the measurement light onto the subject's eye via the optical scanner, and to detect interference light between returning light of the light from the subject's eye and the reference light via the optical scanner. The image forming unit is configured to form a tomographic image of the subject's eye corresponding a first traveling direction of the measurement light deflected by the optical scanner, based on a detection result of the interference light. The intraocular distance calculator is configured to obtain an intraocular distance between predetermined sites of the subject's eye based on the detection result of the interference light. The image correcting unit is configured to correct the tomographic (Continued)

image based on the intraocular distance. The controller is configured to control at least the optical scanner.

25 Claims, 12 Drawing Sheets

(56) References Cited

U.S. PATENT DOCUMENTS

| | | |
|---|---|---|
| 2012/0188510 A1 | 7/2012 | Suehira et al. |
| 2012/0189184 A1 | 7/2012 | Matsumoto et al. |
| 2012/0320339 A1 | 12/2012 | Yonezawa |
| 2012/0330140 A1 | 12/2012 | Yonezawa |
| 2014/0211157 A1* | 7/2014 | Nakahara ............... A61B 3/102 |
| | | 351/246 |
| 2014/0270444 A1 | 9/2014 | Yang et al. |
| 2016/0321828 A1 | 11/2016 | Tachikawa |
| 2018/0289257 A1* | 10/2018 | Ikegami ............... A61B 3/1225 |
| 2018/0353063 A1 | 12/2018 | Uji et al. |

FOREIGN PATENT DOCUMENTS

| | | |
|---|---|---|
| JP | 2012-045102 A | 3/2012 |
| JP | 2012-115575 A | 6/2012 |
| JP | 2012-147977 A | 8/2012 |
| JP | 2012-148003 A | 8/2012 |
| JP | 2013-000223 A | 1/2013 |
| JP | 2016-28781 A | 3/2016 |
| JP | 2016-127900 A | 7/2016 |
| JP | 2016-209182 A | 12/2016 |
| JP | 2017-29611 A | 2/2017 |

OTHER PUBLICATIONS

International Search Report and Written Opinion dated May 28, 2019 for PCT/JP2019/009004 filed on Mar. 7, 2019,11 pages including English Translation of the International Search Report.
Japanese Office Action dated Mar. 8, 2022, in corresponding Japanese Application No. 2018-049744, 9 pp.
Japanese Office Action dated Jun. 20, 2023, in corresponding Japanese Patent Application No. 2022-174890, 5pp.

* cited by examiner

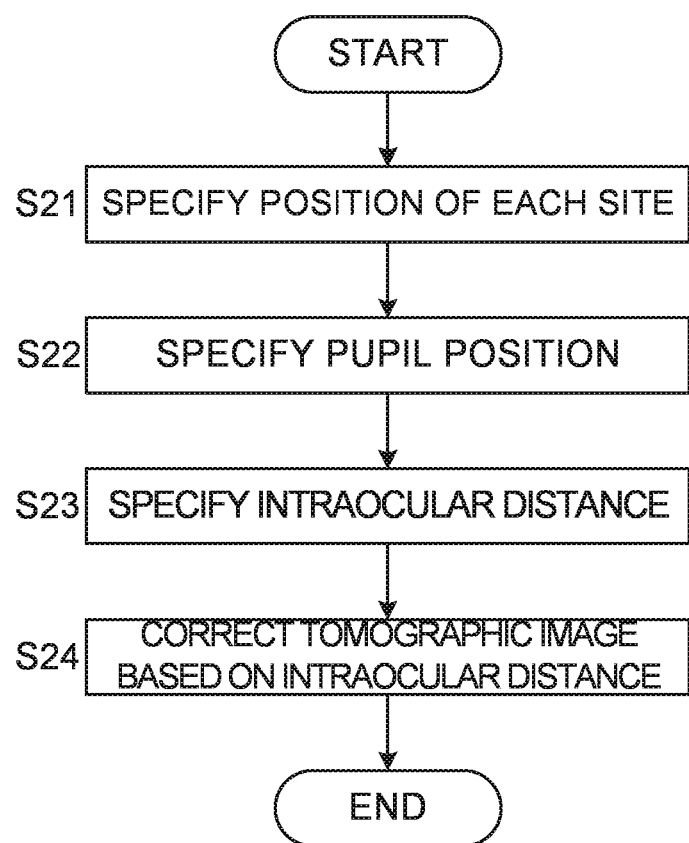

OPHTHALMOLOGIC APPARATUS, AND OPHTHALMOLOGIC INFORMATION PROCESSING APPARATUS

CROSS-REFERENCE TO RELATED APPLICATIONS

The present application is a continuation application of International Patent Application No. PCT/JP2019/009004, filed Mar. 7, 2019, which claims priority to Japanese Patent Application No. 2018-049744, filed Mar. 16, 2018. The contents of these applications are incorporated herein by reference in their entirety.

FIELD

The disclosure relates an ophthalmologic apparatus and an ophthalmologic information processing apparatus.

BACKGROUND

In recent years, attention has been drawn to optical coherence tomography (OCT) which is used to form images representing the surface morphology and the internal morphology of an object using light beams emitted from a laser light source or the like. Since OCT does not have invasiveness to human body as X-ray CT (Computed Tomography) does, development of application of OCT in medical field and biology field is particularly expected. For example, in the ophthalmologic field, apparatuses for forming images of the fundus, the cornea, or the like have been in practical use. Such an apparatus using OCT imaging (OCT apparatus) can be used to observe a variety of sites of a subject's eye. In addition, because of the ability to acquire high precision images, the OCT apparatus is applied to the diagnosis of various eye diseases.

In case of acquiring a tomographic image of a predetermined site in the eye of the subject's eye using OCT, measurement light for scanning the predetermined site is made to enter the eye from a pupil, and the measurement light is deflected around a position near the pupil, for example. The eyeball optical system has different aberrations depending on the deflection direction of the measurement light. Thereby, distortion occurs in the acquired tomographic image. When the angle of view is narrow enough, the influence of distortion is small. However, when the angle of view is wide, the influence of distortion cannot be ignored.

For example, Japanese Unexamined Patent Publication No. 2012-115575 discloses a method of correcting a scanning angle of the measurement light using a scanning means so as to be corrected displacement of the scan length in the tomographic image due to the aberrations of the eyeball optical system.

SUMMARY

One aspect of some embodiments is an ophthalmologic apparatus, including: an optical scanner disposed at an optically substantially conjugate position with a first site of a subject's eye; an interference optical system configured to split light from a light source into reference light and measurement light, to project the measurement light onto the subject's eye via the optical scanner, and to detect interference light between returning light of the measurement light from the subject's eye and the reference light via the optical scanner; and an image forming unit configured to form a tomographic image of the subject's eye corresponding a first traveling direction of the measurement light deflected by the optical scanner, based on a detection result of the interference light obtained by the interference optical system; an intraocular distance calculator configured to obtain an intraocular distance between predetermined sites of the subject's eye based on the detection result of the interference light; an image correcting unit configured to correct the tomographic image formed by the image forming unit, based on the intraocular distance obtained by the intraocular distance calculator; and a controller configured to control at least the optical scanner.

Another aspect according to some embodiments is an ophthalmologic information processing apparatus, including: an image forming unit configured to form a tomographic image of a subject's eye based on data acquired using optical coherence tomography, the optical coherence tomography using an optical scanner disposed at an optically substantially conjugate position with a first site of the subject's eye; an intraocular distance calculator configured to obtain an intraocular distance between predetermined sites of the subject's eye based on the data; and an image correcting unit configured to correct the tomographic image formed by the image forming unit, based on the intraocular distance obtained by the intraocular distance calculator.

BRIEF EXPLANATION OF THE DRAWINGS

FIG. 5 is a flow chart illustrating an example of an operation of the ophthalmologic apparatus according to the embodiments.

DETAILED DESCRIPTION

Figure 1:
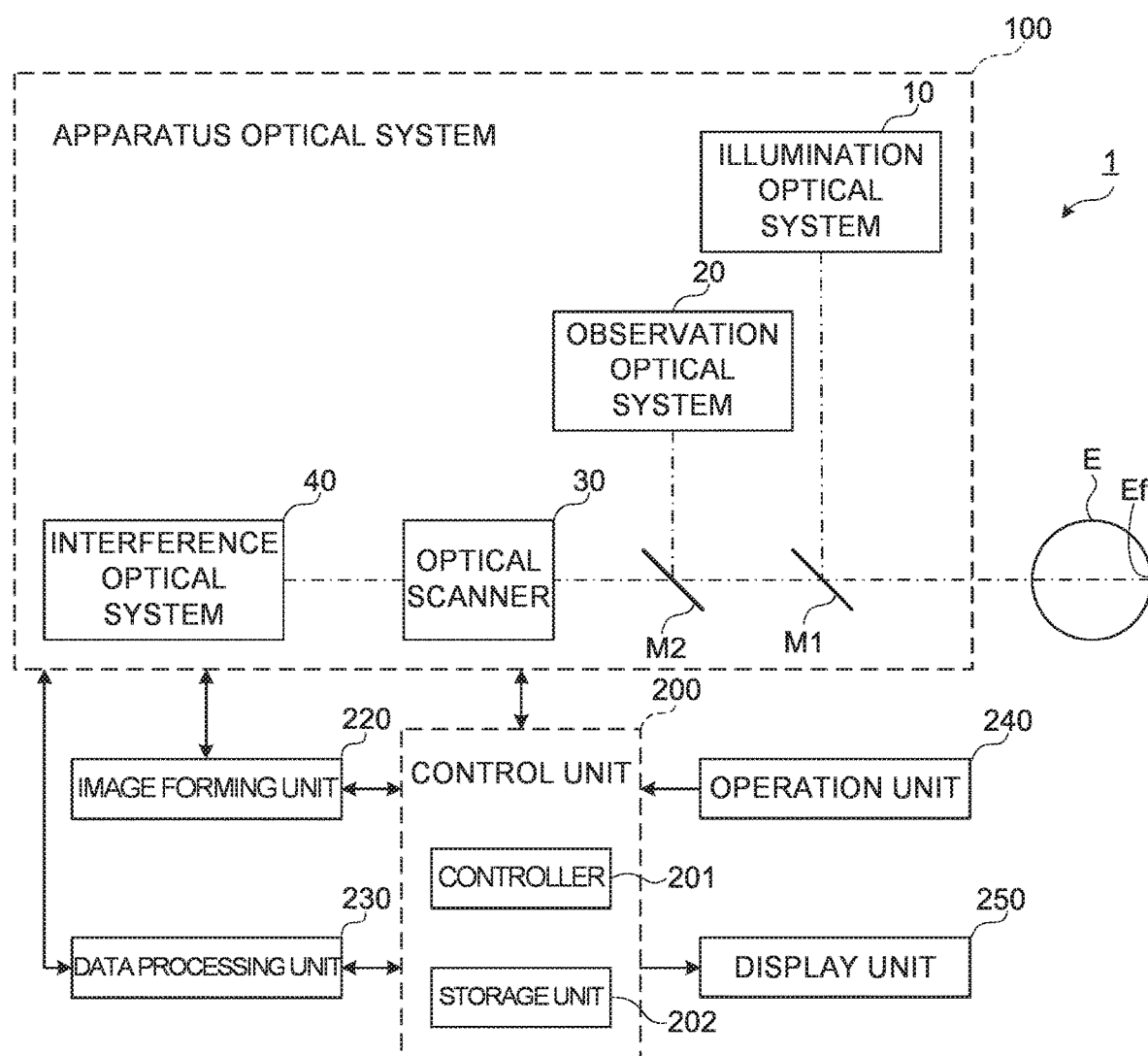
FIG. 1 is a schematic diagram illustrating an example of a configuration of an ophthalmologic apparatus according to embodiments.

In conventional techniques, for a plurality of eyes having various axial lengths, it is necessary to calculate in advance the correction amount of the scanning angle corresponding to all the pixels in the scannable range of the scanning means. Therefore, when the angle of view is large, it is difficult to accurately correct the distortion of the tomographic image for each of subject's eyes having various eyeball optical systems.

According to some embodiments of the present invention, an ophthalmologic apparatus and a ophthalmologic information processing apparatus capable of correcting distortion of a tomographic image of a subject's eye with high accuracy even when an angle of view is large can be provided.

Referring now to the drawings, exemplary embodiments of an ophthalmologic apparatus and an ophthalmologic information processing apparatus according to the present invention are described below. In the embodiments, any of the techniques disclosed in the documents cited in the present specification can be applied to the embodiments below.

An ophthalmologic apparatus according to embodiments can scan a wide range from an anterior segment to a posterior segment of a subject's eye with light beam using optical coherence tomography, and can acquire a distribution of predetermined data (for example, an image, a layer thickness distribution, a lesion distribution). Examples of such an ophthalmologic apparatus include optical coherence tomography using a light source with a high coherence length.

The ophthalmologic information processing apparatus according to the embodiments can obtain an intraocular distance of a subject's eye based on data of the subject's eye acquired using optical coherence tomography performed by the ophthalmologic apparatus described above, and can correct a distortion of a tomographic image of the subject's eye based on the obtained intraocular distance. In some embodiments, at least part of functions of such an ophthalmologic information processing apparatus are included in the ophthalmologic apparatus described above.

The ophthalmologic apparatus according to some embodiments is provided a function of projecting a fixation target onto a fundus. An internal fixation target or an external fixation target can be used as the fixation target.

In the following description, unless otherwise stated, the left-right direction (horizontal direction) viewed from the subject is regarded as a X direction, the up-down direction (vertical direction) is regarded as a Y direction, and the front-back direction (depth direction) is regarded as a Z direction. The X direction, the Y direction, and the Z direction define a three-dimensional orthogonal coordinate system.

<Configuration>

FIG. 1 shows a schematic configuration of an ophthalmologic apparatus according to embodiments. The ophthalmologic apparatus 1 collects data of a subject's eye E by scanning an anterior segment or a posterior segment of the subject's eye E with light using optical coherence tomography, and acquires an image of the subject's eye E based on the collected data. In FIG. 1, a two-dimensional tomographic image of the subject's eye E, a three-dimensional image of the subject's eye E, or a front image of the subject's eye E is acquired.

The ophthalmologic apparatus 1 includes an apparatus optical system 100, a control unit 200, an image forming unit 220, a data processing unit 230, an operation unit 240, and a display unit 250. The apparatus optical system 100 includes an optical system for collecting data of the subject's eye E using optical coherence tomography. The control unit 200 controls the image forming unit 220, the data processing unit 230, the operation unit 240, and the display unit 250.

The apparatus optical system 100 includes an illumination optical system 10, an observation optical system 20, an optical scanner 30, and an interference optical system 40. The apparatus optical system 100 includes optical elements M1, M2 as optical path coupling/separating members for separating an optical path of the optical system described above or coupling with another optical system.

The optical element M1 couples an optical path of the illumination optical system 10 and optical paths of the other optical systems (observation optical system 20, optical scanner 30, interference optical system 40), or separates an optical path of returning light from the subject's eye E into the optical path of the illumination optical system 10 and the optical paths of the other optical systems. It is preferred that the optical element M1 couples the illumination optical system 10 and the other optical systems so that an optical axis of the illumination optical system 10 is substantially coaxial with optical axes of the other optical systems.

The optical element M2 couples an optical path of the observation optical system 20 and optical paths of the other optical systems (optical scanner 30, interference optical system 40), or separates the optical path of returning light from the subject's eye E into the optical path of the observation optical system 20 and the optical paths of the other optical systems. It is preferred that the optical element M2 couples the observation optical system 20 and the other optical systems so that an optical axis of the observation optical system 20 is substantially coaxial with optical axes of the other optical systems.

In the apparatus optical system 100 according to some embodiments, an objective lens is arranged between the subject's eye E and the optical element M1. That is, the apparatus optical system 100 may include an objective lens common to each optical system.

(Illumination Optical System 10)

The illumination optical system 10 illuminates an anterior segment or a fundus Ef of the subject's eye E. The illumination optical system 10 includes an illumination light source, a lens, and the like.

Illumination light from the illumination optical system 10 is reflected by the optical element M1, and is guided to the subject's eye E. Returning light (reflected light) of the illumination light from the subject's eye E is transmitted through the optical element M1, is reflected by the optical element M2, and is guided to the observation optical system 20.

In some embodiments, the optical element M1 is a perforated mirror which couples the optical path of the illumination optical system 10 and the optical paths of the other optical systems. In the perforated mirror, a hole part through which an optical axis of the optical scanner 30 (interference optical system 40) passes is formed. For example, the hole part of the perforated mirror is disposed at a position optically substantially conjugate with a pupil of the subject's eye E. The illumination light from the illumination optical system 10 is reflected on a peripheral part of the hole part formed in the perforated mirror, and is guided to the subject's eye E. The returning light of the illumination light from the subject's eye E passes through the hole part formed in the perforated mirror, is reflected by the optical element M2, and is guided to the observation optical system 20.

In some embodiments, the optical element M2 is a dichroic mirror.

(Observation Optical System 20)

The observation optical system 20 is used for observing the anterior segment or the fundus Ef of the subject's eye E illuminated using the illumination light from the illumination optical system 10.

The observation optical system 20 includes at least one of an eyepiece and an imaging element. The eyepiece is used for observing the subject's eye E with the naked eye(s). The imaging element is used for acquiring a front image of the subject's eye E. The control unit 200 that has received a signal from the imaging element controls the display unit 250 to display the image acquired using the imaging element on a display (not shown) or the like.

(Optical Scanner 30)

The optical scanner 30 deflects light from the interference optical system 40, and guides the deflected light to the optical element M2. The optical scanner 30 is disposed at an optically substantially conjugate position with a predetermined site in the subject's eye E. Examples of the predetermined site include a center position of the pupil and a position of the center of gravity of the pupil. Thereby, measurement light from the interference optical system 40 is deflected with the predetermined site in the subject's eye E as a scan center position. In some embodiments, the optical scanner 30 can be disposed at an optically substantially conjugate position with a of arbitrary site in the subject's eye E.

In some embodiments, the optical scanner 30 includes a uniaxial deflecting member or a biaxial deflecting member orthogonal to each other. Examples of the deflecting member include a galvano mirror, a polygon mirror, a rotating mirror, a dove prism, a double dove prism, a rotation prism, and a MEMS mirror scanner. When the biaxial deflecting member is used, a deflecting member for high speed scanning (for example, the polygon mirror) and a deflecting member for low speed scanning (for example, the galvano mirror) can be combined. The optical scanner 30 may further include an optical element for projecting the deflected light onto the subject's eye E.

The optical scanner 30 can deflect light from the interference optical system 40 under the control of the control unit 200 described later. Thereby, the irradiated position of the light from interference optical system 40 in the subject's eye E can be changed in at least one of the X direction and the Y direction.

The light deflected by the optical scanner 30 is transmitted through the optical element M2, is guided to the optical element M1, is transmitted through the optical element M1, and is guided to the subject's eye E. Returning light from the subject's eye E is transmitted through the optical element M1, is transmitted through the optical element M2, and is guided to the optical scanner 30. In case that the optical element M1 is a perforated mirror, the light from the optical scanner 30 passes through the hole part formed in the perforated mirror, and the returning light from the subject's eye E also passes through the hole part and is guided to the optical element M2.

(Interference Optical System 40)

The interference optical system 40 splits light from a light source into measurement light and reference light, and guides interference light to a detector. The interference light is obtained by superimposing the reference light and returning light of the measurement light from the subject's eye E, the measurement light having passed through the optical scanner 30. The interference optical system 40 includes an optical system which is capable of performing, for example, a swept source type or a spectral domain type OCT (Optical Coherence Tomography). In the following, a case that the interference optical system 40 according to the embodiments is capable of performing swept source type OCT will be described.

The interference optical system 40 according to the embodiments includes an OCT light source. The OCT light source is a wavelength swept type (i.e., a wavelength scanning type) light source capable of sweeping (scanning) the wavelengths of emitted light. For example, a laser light source, which includes a resonator and emits light having a predetermined center wavelength, is used as the wavelength swept type light source. The wavelength swept type light source temporally changes the output wavelength in the near infrared wavelength band which cannot be visually recognized by the human eye.

The OCT light source according to the embodiments is a wavelength swept light source with high coherence (long coherence length). The OCT light source according to the embodiments can change the sweep frequency (sweep speed) of the wavelength, the sweep start wavelength, the sweep end wavelength, the sweep wavelength range, and the like, under the control of the control unit 200 described later. For example, the control unit 200 can cause the image forming unit 220 to form a plurality of tomographic images having different depth ranges by changing the sweep frequency.

In some embodiments, light output from the OCT light source is, for example, near infrared light having a center wavelength of about 1040 nm to 1060 nm (for example, 1050 nm) and a wavelength width of about 50 nm.

Light output from the OCT light source is guided through an optical fiber to a fiber coupler, and is divided into the measurement light and the reference light. The measurement light is guided through an optical fiber, is emitted from the end of the fiber, is collimated into a parallel light flux by a collimator lens, and is guided to the optical scanner 30. The end of the fiber of this optical fiber is located at the fundus conjugate position or near the position. The fundus conjugate position is optically substantially conjugate with the fundus Ef of the subject's eye E. The measurement light is deflected by the optical scanner 30, is transmitted through the optical element M2, is transmitted through the optical element M1, and is guided to the subject's eye E. For example, the measurement light irradiated onto the fundus Ef is scattered and reflected at the measurement site(s) such as the fundus Ef. The scattered and reflected light may be sometimes referred to as returning light of the measurement light. The returning light of the measurement light travels through the same path in the opposite direction, and is thereby guided to the fiber coupler described above.

On the other hand, the reference light is guided through an optical fiber, is reflected by a reference mirror movable along the optical path of the reference light. The reflected light is again guided to the fiber coupler described above. In some embodiments, a polarization adjuster (polarization controller), an optical element for dispersion compensation (pair prism, etc.), an optical element for polarization correction (wavelength plate, etc.), or an optical attenuator (attenuator) may be provided on the optical path of the reference light. The polarization adjuster applies external stress to the looped optical fiber, for example, to thereby adjust the polarization condition of the reference light guided through the optical fiber. The optical attenuator adjusts the amount of the reference light guided through the optical fiber under the control of the control unit 200.

The returning light of the measurement light and the reference light reflected by the reference mirror enter the fiber coupler described above. The fiber coupler superposes the returning light of the measuring light on the reference light. Interference light thus generated is guided to a detector through an optical fiber. At this time, a pair of interference light is generated by another fiber coupler. The another fiber coupler generates the pair of interference light by branching the interference light at a predetermined branching ratio (for example, 50:50). The pair of interference light is detected by the detector (balanced photodiode).

The detector sends a detection result (detection signal) of the pair of interference light to a data acquisition system (DAQ) (not shown). The DAQ is fed with a clock from the OCT light source. This clock is generated in synchronization with the output timing of each wavelength swept within a predetermined wavelength range by the wavelength swept type light source. The DAQ performs sampling of the detection signal based on the clock. The sampling result is sent to the image forming unit 220 for forming an OCT image.

The apparatus optical system 100 according to some embodiments includes at least one of an alignment system for performing alignment of the apparatus optical system 100 with respect to the subject's eye E and a focus system for performing focus of the apparatus optical system 100 with respect to the subject's eye E.

(Control Unit 200)

The control unit 200 includes a controller 201 and a storage unit 202. The functions of the controller 201 are implemented by a processor, for example. In this specification, the function of the processor is implemented by a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). The storage unit 202 stores, in advance, a computer program for controlling the ophthalmologic apparatus 1. The computer program includes, for example, various light source control programs, optical scanner control program, various detector control programs, image forming program, data processing program, program for user interface, and the like. The controller 201 operates according to the computer programs, and thereby the control unit 200 performs the control process.

The storage unit 202 stores various types of data. Examples of the data stored in the storage unit 202 include data of the subject's eye such as OCT data acquired using interference optical system 40, OCT images, and subject's eye information. The subject's eye information includes subject information such as patient ID and name, identification information of the left eye/right eye, and information of electronic medical record.

(Image Forming Unit 220)

The image forming unit 220 forms a tomographic image (A scan image) of the subject's eye E along a traveling direction of the measurement light deflected by the optical scanner 30, based on a detection result of the interference light obtained by the interference optical system 40. The image forming unit 220 can form a plurality of tomographic images corresponding to a plurality of traveling directions of the measurement light deflected by the optical scanner 30. That is, the image forming unit 220 can form a first tomographic image of the subject's eye E and a second tomographic image of the subject's eye E. The first tomographic image corresponds to a first traveling direction. The second tomographic image corresponds to a second traveling direction of the measurement light deflected by the optical scanner 30. The image forming unit 220 forms the tomographic image of the subject's eye E based on a light receiving signal input from the detector and a pixel position signal input from the control unit 200, for example as is the case with conventional OCT.

Further, the image forming unit 220 can form a B scan image or a C scan image from the tomographic image(s) (A scan image(s)) of the subject's eye E along the traveling direction(s) of the measurement light, using a known method. For example, the image forming unit 220 can apply Fourier transform and the like to the spectral distribution based on the detection result of the interference light, for example, every series of wavelength scans (every A-line) to form the reflection intensity profile in each A-line. The image forming unit 220 can form image data by imaging the reflection intensity profile in each A-line.

The image forming unit 220 includes a storage device that stores a program for forming image and a processor that operates in accordance with the program for forming image.

(Data Processing Unit 230)

The data processing unit 230 performs various types of data processing (image processing) and/or analysis processing on the light receiving result obtained using the apparatus optical system 100, under the control of the control unit 200. For example, the data processing unit 230 performs various correction processes such as brightness correction and dispersion correction of images. In some embodiments, the data processing unit 230 performs data processing such as image analysis, image evaluation, diagnostic support. Further, the data processing unit 230 performs various kinds of image processing and various kinds of analysis processing on tomographic images. The data processing unit 230 can form volume data (voxel data) of the subject's eye E by performing known image processing such as interpolation processing for interpolating pixels between tomographic images. In the case of displaying an image based on the volume data, the data processing unit 230 performs rendering processing on the volume data so as to form a pseudo three-dimensional image viewed from a specific line-of-sight direction.

The data processing unit 230 obtains an intraocular distance between predetermined sites in the subject's eye E based on the detection result of the interference light acquired by the interference optical system 40, and corrects the tomographic image formed by the image forming unit 220, based on the obtained intraocular distance.

Figure 2:
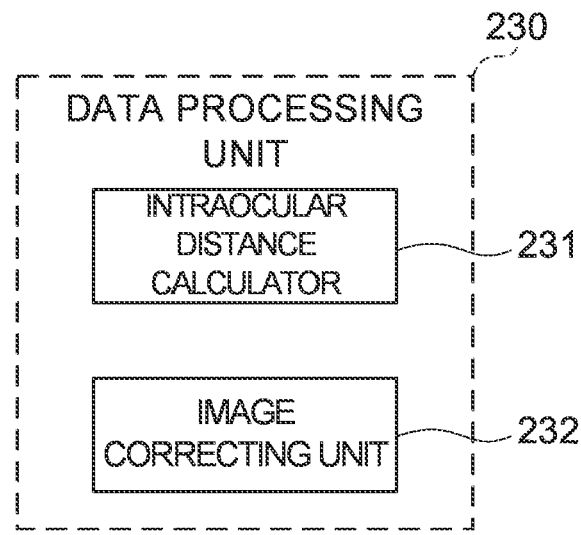
FIG. 2 is a schematic diagram illustrating an example of a configuration of the ophthalmologic apparatus according to the embodiments.

FIG. 2 shows a block diagram of an example of the configuration of the data processing unit 230 of FIG. 1. The data processing unit 230 includes an intraocular distance calculator 231 and an image correcting unit 232.

The intraocular distance calculator 231 obtains the intraocular distance between predetermined sites in the subject's eye based on the detection result of the interference light acquired by the interference optical system 40. For example, the intraocular distance calculator 231 specifies peak positions of the interference light corresponding to the predetermined sites in the eye by analyzing the detection result of the interference light acquired by the interference optical system 40, and obtains the intraocular distance described above based on a distance between the specified peak positions. Examples of the intraocular distance between the predetermined sites include an axial length, a distance from a scan center position of the measurement light, which is set at the center of the pupil, or the like, to a retina. In case that the axial length is obtained as the intraocular distance, the intraocular distance calculator 231 obtains the axial length based on a distance from a peak position corresponding to a corneal apex to a peak position corresponding to the retina. In case that the distance from the scan center position of the measurement light to the retina is obtained as the intraocular distance, the intraocular distance calculator 231 specifies the scan center position, and obtains the intraocular distance based on a distance from the specified scan center position to a peak position corresponding to the retina.

The image correcting unit 232 corrects the tomographic image according to the angle of view changed by the optical scanner 30. The optical scanner 30 changes the angle of view by changing a deflection angle of the measurement light. Thereby, the tomographic image can be corrected according to the scan length that differs depending on the deflection angle (scan angle) of the measurement light.

Specifically, the image correcting unit 232 corrects the tomographic image formed by the image forming unit 220, based on the intraocular distance obtained by the intraocular distance calculator 231, to generate a corrected image. Thereby, the scan length that differs depending on the deflection angle (scan angle) of the measurement light can be obtained substantially, and the tomographic image can be corrected according to the obtained scan length. Therefore, the tomographic image can be corrected according to the aberrations of the eyeball optical system of the subject's eye E. Thereby, the distortion of the tomographic image according to the subject's eye E can be corrected with high accuracy.

In some embodiments, the image correcting unit 232 corrects the tomographic image for each A scan, and generates the corrected image in which a corrected plurality of tomographic images is arranged along a direction corresponding to an optical axis direction of the interference optical system 40. Examples of the direction corresponding to the optical axis direction of the interference optical system 40 (traveling direction of the measurement light) include a direction orthogonal to the optical axis. Examples of the correction processing performed by the image correcting unit 232 include pixel value composition processing, thinning processing, and decompression processing which are performed based on the intraocular distance. Thereby, the B scan image corrected according to the aberrations of the eyeball optical system of the subject's eye E can be acquired. In some embodiments, the image correcting unit 232 corrects the tomographic image based on the intraocular distance obtained in units of a plurality of A scans by the intraocular distance calculator 231.

In some embodiments, the image correcting unit 232 corrects each of a plurality of tomographic images so that the distance between the predetermined sites in each of the tomographic images becomes a constant value. Thereby, the B image (C scan image) in which the aberrations of the eyeball optical system of the subject's eye E is compensated can be acquired.

In some embodiments, the image correcting unit 232 corrects each of a plurality of A scan images at different deflection angles based on the intraocular distance(s). The image correcting unit 232 generates the corrected image in which each of a corrected plurality of A scan images is arranged along a scan direction of each of the A scan images, the scan direction(s) passing through the scan center position. That is, the image correcting unit 232 corrects each of the plurality of tomographic images based on the intraocular distance(s), the tomographic images corresponding to a plurality of traveling directions of the measurement light, and generates the corrected image in which each of the corrected plurality of tomographic images is arranged along the scan direction of each tomographic image, the scan direction passing through the scan center position. For example, the image correcting unit 232 corrects each of a first tomographic image and a second tomographic image based on the intraocular distance, the first tomographic image corresponding to a first traveling direction of the measurement light, the second tomographic image corresponding to a second traveling direction of the measurement light. The image correcting unit 232 generates the corrected image in which the corrected first tomographic image is arranged along a direction passing through the scan center position and corresponding to the first traveling direction and the corrected second tomographic image is arranged along a direction passing through the scan center position and corresponding to the second traveling direction. Thereby, the corrected image corresponding to the shape in the eye of the subject's eye E can be acquired.

The data processing unit 230 includes a controller and a storage unit, similar to the control unit 200. The controller operates in accordance with the computer program stored in advance in the storage unit. Thereby, the data processing is executed.

In some embodiments, the ophthalmologic information processing apparatus performs processing described above on the detection result of the interference light obtained using the apparatus optical system 100. For example, the ophthalmologic information processing apparatus includes the image forming unit 220, the data processing unit 230, the operation unit 240, the display unit 250, and a control unit for controlling these units. The control unit included in the ophthalmologic information processing apparatus has functions of the image forming unit 220, the data processing unit 230, the operation unit 240, and the display unit 250 among the functions described above of the control unit 200.

(Operation Unit 240)

The operation unit 240 is used by the user to input instructions to the ophthalmologic apparatus 1. The operation unit 240 may include a known operation device used for a computer. For example, the operation unit 240 may include a pointing device such as a mouse, a touch pad or a track ball. Further, the operation unit 240 may include a keyboard, a pen tablet, a dedicated operation panel, or the like.

(Display Unit 250)

The display unit 250 includes a display such as a liquid crystal display. The display unit 250 displays various information such an images, under the control of the control unit 200. Note that the display unit 250 and the operation unit 240 need not necessarily be formed as separate unit. For example, a device like a touch panel, which has a display function integrated with an operation function, can be used.

The ophthalmologic apparatus 1 according to some embodiments apparatus is provided with an optical system movement unit (not shown) for moving the apparatus optical system 100 three-dimensionally (in the X direction, the Y direction, and the Z direction). Thereby, the subject's eye E and the apparatus optical system 100 can be moved relatively. The optical system movement unit may move only a part of the optical system in the apparatus optical system 100 shown in FIG. 1. The optical system movement unit is provided with a holding member that holds the optical system to be moved (for example, the apparatus optical system 100), an actuator that generates a driving force for moving the holding member, and a transmission mechanism that transmits the driving force from the actuator to the holding member. The actuator includes a pulse motor, for example. The transmission mechanism includes a combination of gears, a rack and pinion, and the like, for example. The control unit 200 is capable of controlling the optical system movement unit to three-dimensionally move the optical system installed in the apparatus optical system 100. For example, this control is used for alignment and tracking. Here, the tracking is to move the apparatus optical system 100 according to the movement of the subject's eye E. To perform tracking, alignment and focusing are performed in advance. The tracking is performed by moving the apparatus optical system 100 in real time according to the position and orientation of the subject's eye E based on the image obtained by shooting a movie of the subject's eye E, thereby maintaining a suitable positional relationship in which alignment and focusing are adjusted.

The scan center position or the center of the pupil is an example of the "first site" according to the embodiments. The image forming unit 220 is an example of the "image forming unit" according to the embodiments. The control unit 200 or the controller 201 is an example of the "controller" according to the embodiments. The optical scanner 30 is an example of the "angle-of-view change unit" according to the embodiments.

Operation Example

An example of the operation of the ophthalmologic apparatus 1 according to the embodiments will be described.

Figure 3:
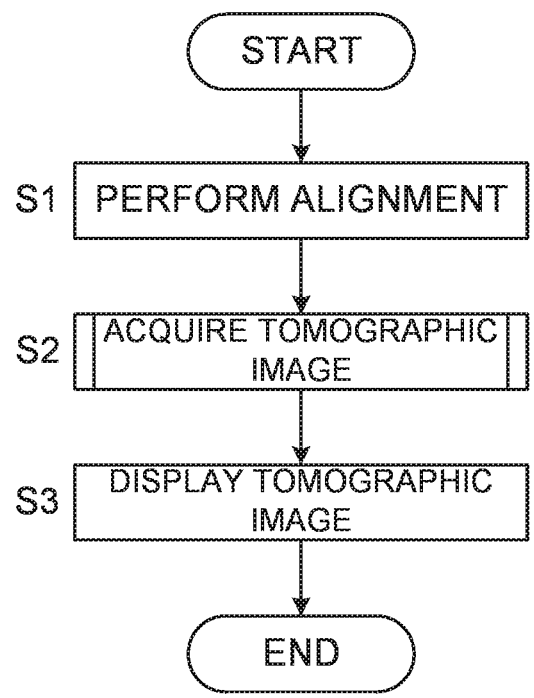
FIG. 3 is a flow chart illustrating an example of an operation of the ophthalmologic apparatus according to the embodiments.
Figure 4:
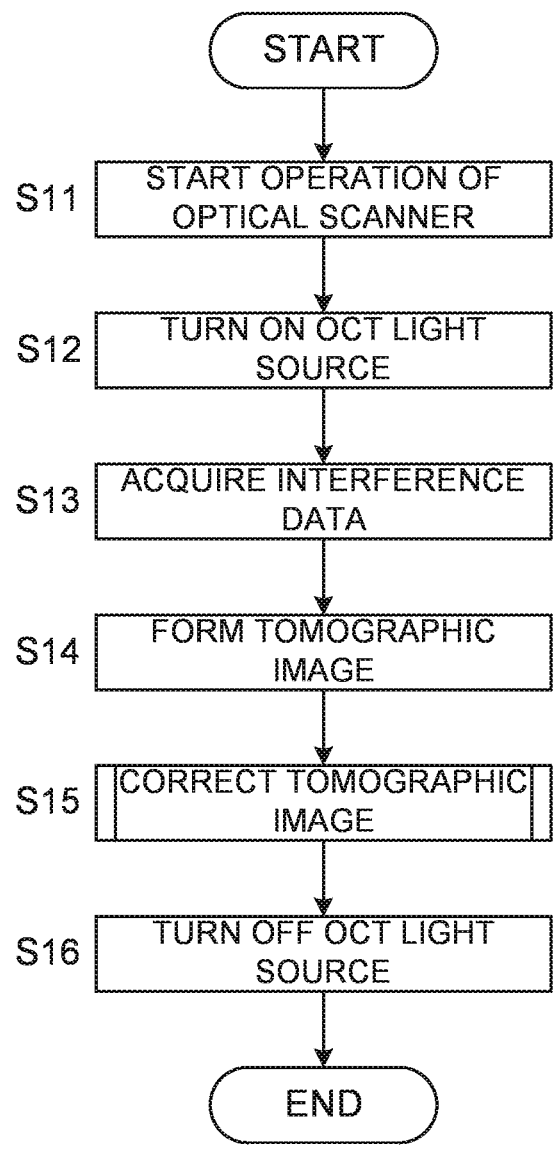
FIG. 4 is a flow chart illustrating an example of an operation of the ophthalmologic apparatus according to the embodiments.

FIG. 3, FIG. 4, and FIG. 5 show an outline of an example of the operation of the ophthalmologic apparatus 1 according to the embodiments. FIG. 3 shows a flow chart of an example of the operation of the ophthalmologic apparatus 1 according to the embodiments. FIG. 4 shows a flow chart of an example of the operation of step S2 in FIG. 3. FIG. 5 shows a flow chart of an example of the operation of step S15 in FIG. 4. The storage unit 202 in the control unit 200 stores computer programs for realizing the processing shown in FIGS. 3 to 5. The controller 201 in the control unit 200 operates according to the computer programs, and thereby the controller 201 performs processing shown in FIGS. 3 to 5.

(S1: Perform Alignment)

First, the control unit 200 controls the optical system movement unit to move the apparatus optical system 100 to an initial position. After then, the control unit 200 performs alignment for position matching of the apparatus optical system 100 with respect to the subject's eye E.

For example, the control unit 200 causes the fundus image (the front image of the fundus Ef) of the subject's eye E acquired using the observation optical system 20 to be displayed on the display of the display unit 250. The control unit 200 can control the optical system movement unit so as to move the apparatus optical system 100 in a direction designated by the user using the operation unit 240. In this case, the observation optical system 20 acquires the fundus image of the subject's eye E illuminated by the illumination optical system 10.

In some embodiments, the control unit 200 causes the anterior segment image of the subject's eye E acquired using the anterior segment imaging system (not shown) to be displayed on the display of the display unit 250. The control unit 200 controls the optical system movement unit so as to move the apparatus optical system 100 in a direction designated by the user using the operation unit 240.

In some embodiments, the control unit 200 performs position matching of the apparatus optical system 100 with respect to the subject's eye E, by projecting light from an alignment light source (not shown) onto the subject's eye E to control the optical system movement unit based on an image corresponding to returning light of the light.

In some embodiments, the control unit 200 causes the anterior segment of the subject's eye E to be photographed from different directions using two or more cameras (not shown), and causes the position of the subject's eye E to be specified from two or more images with parallax. The control unit 200 performs position matching of the apparatus optical system 100 with respect to the subject's eye E, by controlling the optical system movement unit based on the specified position of the subject's eye E.

The control unit 200 can perform focus adjustment and start tracking after the alignment is completed.

The control unit 200 can specify an in-focus state (degree of blur) of the fundus image acquired by observation optical system 20, and can perform focus adjustment by moving the apparatus optical system 100 etc. so that the specified in-focus state becomes a desired in-focus state. Alternatively, the control unit 200 may photograph the anterior segment from different directions each other using the two or more cameras, may specify the in-focus state from the two or more images with parallax, and may obtain a movement amount in the Z direction of the apparatus optical system 100 so that the specified in-focus state becomes a desired in-focus state.

Further, the control unit 200 causes the images of the subject's eye E to be repeatedly acquired using the observation optical system 20, and causes the characteristic site in the image acquired at a predetermined timing to be specified. The control unit 200 can perform tracking by controlling the optical system movement unit so as to cancel a displacement amount when the specified position of the characteristic site is changed.

(S2: Acquire Tomographic Image)

Next, the control unit 200 performs OCT using the interference optical system 40, and causes the image forming unit 220 to form a tomographic image of the subject's eye E. In step S2, the intraocular distance of the subject's eye E is obtained as described above, and the tomographic image corrected based on the obtained intraocular distance is acquired. Details of step S2 will be described later.

(S3: Display Tomographic Image)

Subsequently, the control unit 200 causes the tomographic image acquired in step S2 to be displayed on the display of the display unit 250. This terminates the operation of the ophthalmologic apparatus 1 (END).

In step S2 in FIG. 3, processing as shown in FIG. 4 is performed. In FIG. 4, it is assumed that scan conditions (scan start position, scan end position, scan area, scan pattern) have been already set for the optical scanner 30. Further, it assumed that wavelength sweep conditions (sweep start wavelength, sweep end wavelength, sweep wavelength range) have been already set for the OCT light source in the interference optical system 40.

(S11: Start Operation of Optical Scanner)

The control unit 200 controls the optical scanner 30 to start the deflection operation of the measurement light. The optical scanner 30 starts the deflection operation within the deflection angle range corresponding to the scan conditions set in advance.

(S12: Turn on OCT Light Source)

The control unit 200 controls the OCT light source in the interference optical system 40 to start emitting the output light. The OCT light source starts the wavelength sweeping operation of the output light corresponding to the wavelength sweep conditions set in advance.

(S13: Acquire Interference Data)

The interference optical system 40 projects the measurement light onto the subject's eye E via the optical scanner 30, the measurement light being generated based on light from the OCT light source as described above, generates the interference light between the reference light and the returning light of the measurement light from the subject's eye E, and detects the generated interference light. The detection result of the interference light is acquired as interference data.

(S14: Form Tomographic Image)

The control unit 200 causes the image forming unit 220 to form the tomographic image of the subject's eye E using a known method, based on the interference data acquired in step S13. In step S14, at least one B scan image is formed.

(S15: Correct Tomographic Image)

The control unit 200 performs correction corresponding to the aberrations of the eyeball optical system of the subject's eye E on the tomographic image formed in step S14, by controlling the data processing unit 230. Details of step S15 will be described later.

(S16: Turn Off OCT Light Source)

The control unit 200 controls the OCT light source in the interference optical system 40 to stop emitting the output light. The OCT light source stops the wavelength sweeping operation of the output light. This terminates the processing of step S2 in FIG. 3 (END).

In step S15 in FIG. 4, processing as shown in FIG. 5 is performed.

(S21: Specify Position of Each Site)

The control unit 200 causes the data processing unit 230 to analyze the tomographic image acquired in step S14 in FIG. 4. The intraocular distance calculator 231 specifies a position in the Z direction (depth direction) of each site for each A scan line. For example, the intraocular distance calculator 231 specifies the position in the Z direction of each site for each A scan line, based on the B scan image acquired in step S14.

Figure 6A:
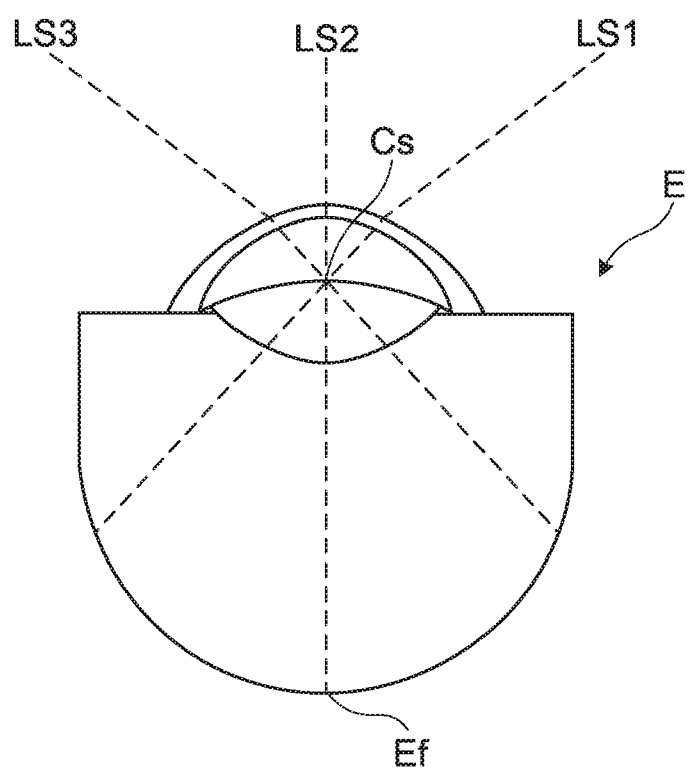
FIG. 6A is a schematic diagram for explaining the operation of the ophthalmologic apparatus according to the embodiments.
Figure 6B:
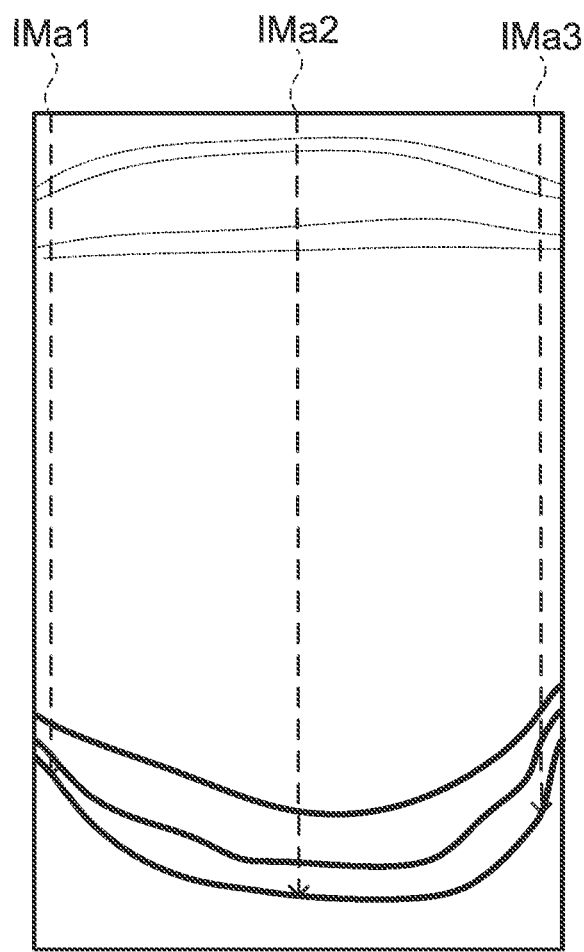
FIG. 6B is a schematic diagram for explaining the operation of the ophthalmologic apparatus according to the embodiments.

FIGS. 6A and 6B show diagrams explaining the operation of the intraocular distance calculator 231 according to the embodiments. FIG. 6A schematically shows the path of the measurement light incident on the subject's eye E. FIG. 6B shows an example of the tomographic image obtained by scanning with the measurement light incident on the subject's eye E through the path shown in FIG. 6A.

The measurement light deflected by the optical scanner 30 is incident on the pupil of the subject's eye E at various incident angles as shown in FIG. 6A. The measurement light incident on the subject's eye E is projected toward each part in the eye around the scan center position Cs set at the center of the pupil, for example.

For example, the interference data obtained using the measurement light LS1 in FIG. 6A is used for generating the A scan image IMa1 in FIG. 6B. In the same manner, the interference data obtained using the measurement light LS2 is used for generating the A scan image IMa2. The interference data obtained using the measurement light LS3 is used for generating the A scan image IMa3.

In the present embodiments, the intraocular distance calculator 231 specifies a corneal anterior surface position CF corresponding to an anterior surface of a cornea, a corneal posterior surface position CB corresponding to a posterior surface of the cornea, a lenticular anterior surface position LF corresponding to an anterior surface of a lens, a lenticular posterior surface position LB corresponding to a posterior surface of the lens, and a retinal position R corresponding to a retina, for each A scan line.

Figure 7:
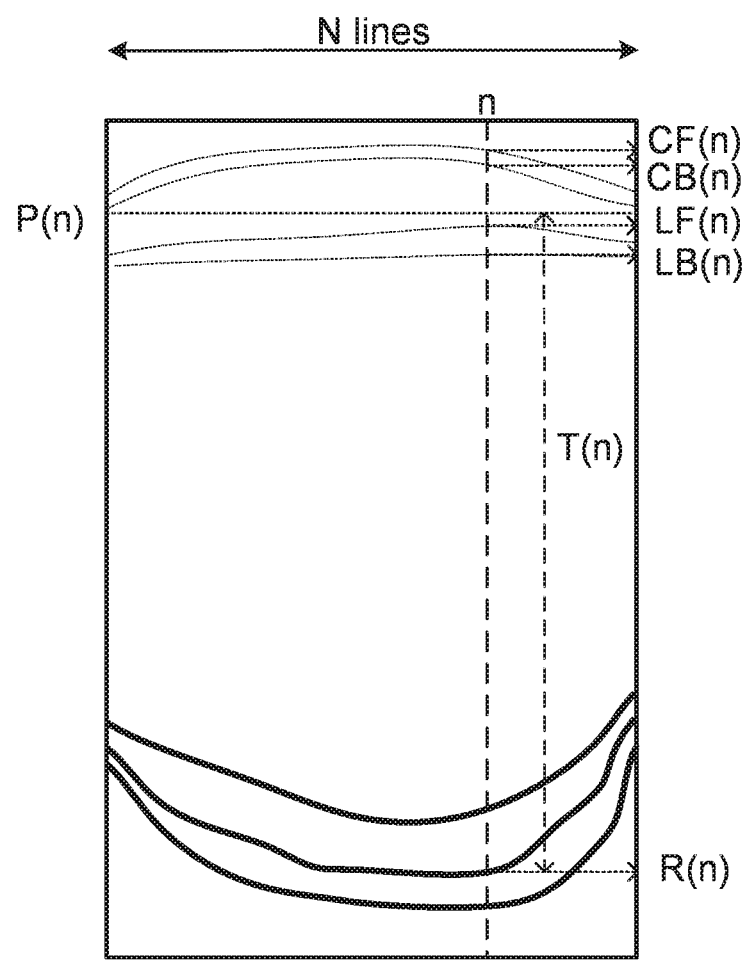
FIG. 7 is a schematic diagram for explaining the operation of the ophthalmologic apparatus according to the embodiments.

FIG. 7 schematically shows an example of the tomographic image acquired in step S14 in FIG. 4. In step S14, it is assumed that the B scan image composed of A scan images for N (N is an integer of 2 or more) lines is acquired. In FIG. 7, the vertical direction represents the A scan direction, and the horizontal direction represents the B scan direction. It should be noted that a pupil position (the center position of the pupil) P is illustrated, in FIG. 7.

When a position of the A scan line is represented by n ($1 \leq n \leq N$, n is an integer), the intraocular distance calculator 231 specifies the corneal anterior surface position CF(n), the corneal posterior surface position CB(n), the lenticular anterior surface position LF(n), the lenticular posterior surface position LB(n), and the retinal position R(n), for the A scan line "n".

(S22: Specify Pupil Position)

The intraocular distance calculator 231 specifies the pupil position P from a position of each site specified in step S21.

The intraocular distance calculator 231 can specify the pupil position P for each A scan line. For example, the intraocular distance calculator 231 specifies the pupil position P(n) from the corneal anterior surface position CF(n), the lenticular anterior surface position LF(n), and the lenticular posterior surface position LB(n), based on the positional relationship of each site in the schematic eye.

(S23: Specify Intraocular Distance)

The intraocular distance calculator 231 specifies the intraocular distance from a position of each site specified in step S21 and the pupil position specified in step S22. The intraocular distance calculator 231 can specify the intraocular distance for each A scan line. For example, the intraocular distance calculator 231 specifies the intraocular distance T from the pupil position P to the retinal position R, as an axial length. In this case, the intraocular distance calculator 231 specifies the intraocular distance T(n) between the pupil position P(n) and the retinal position R(n).

(S24: Correct Tomographic Image Based on Intraocular Distance)

The image correcting unit 232 corrects the tomographic image acquired in step S14, based on the intraocular distance specified in step S23. The image correcting unit 232 can correct each A scan image acquired in step S14, so that the intraocular distance T(n) in each of A scan images becomes a constant value. In some embodiments, the intraocular distance calculator 231 obtains an average value of the intraocular distance T (n) in the B scan direction. The image correcting unit 232 can correct each A scan image acquired in step S14, so as to become the average value of the obtained intraocular distance T(n). This terminates the processing of step S15 in FIG. 4 (END).

Figure 8:
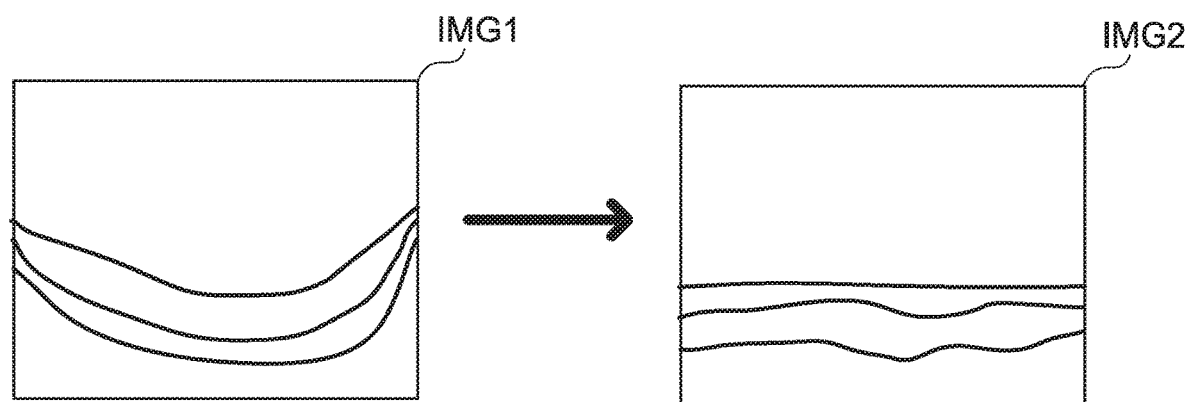
FIG. 8 is a schematic diagram for explaining the operation of the ophthalmologic apparatus according to the embodiments.

FIG. 8 shows a diagram explaining the operation of the ophthalmologic apparatus 1 according to the embodiments. FIG. 8 schematically shows an example of the corrected image when the tomographic image is corrected so that the intraocular distance becomes a constant value.

The tomographic image IMG1 acquired in step S14 in FIG. 4 is corrected to the tomographic image IMG2 by performing the image correction processing in step S24. In step S24, the corrected image, in which the intraocular distance from the pupil position P to the retinal position R is a constant in each A scan image, is generated. In this case, the image is corrected so that the intraocular distances become a constant value regardless of the deflection angle of the measurement light. Thereby, the tomographic structure of the subject's eye E can be easily grasped.

Modification Example

First Modification Example

The processing performed by the intraocular distance calculator 231 is not limited to the processing shown in FIG. 7.

Figure 9:
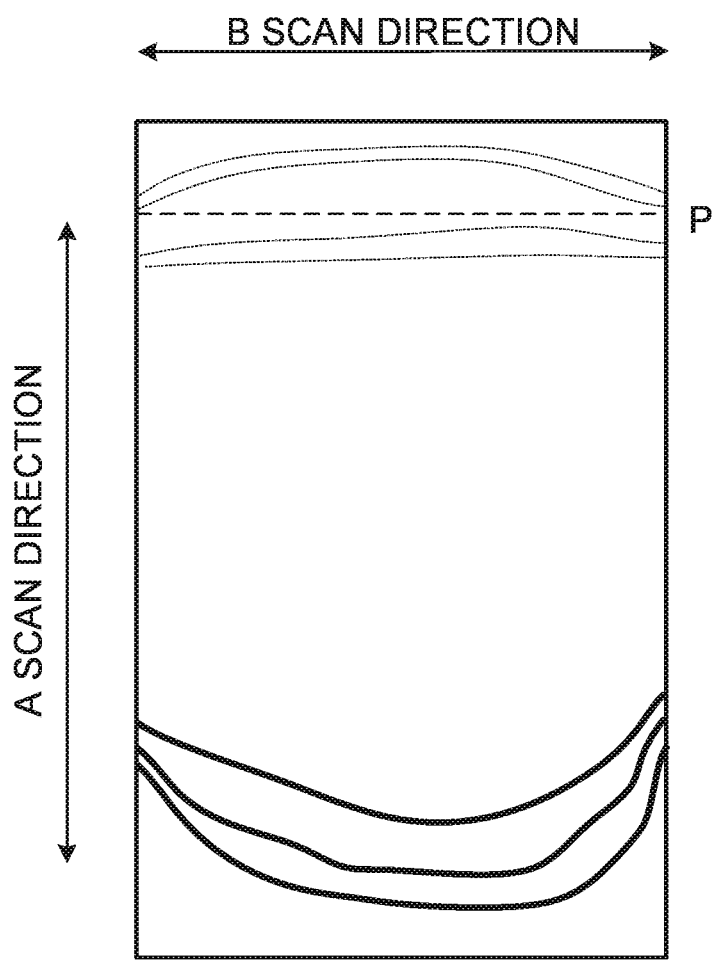
FIG. 9 is a schematic diagram for explaining the operation of the ophthalmologic apparatus according to a modification example of the embodiments.

FIG. 9 shows a diagram explaining the operation of the intraocular distance calculator according to the first modification example of the embodiments.

The intraocular distance calculator according to the first modification example obtains a variance value for each line in the B scan direction and specifies a line having a luminance value equal to or larger than a threshold and having a minimum variance value as the pupil position(s) P, for the tomographic image acquired in step S14. The intraocular distance calculator specifies the retinal position R(n) in each A scan line, in the same manner as the embodiments.

The intraocular distance calculator obtains the distance Q between the specified pupil position P and the retinal position R, and obtains the intraocular distance T based on the obtained distance Q and a refractive index of medium through which measurement light passes. For example, the intraocular distance calculator can obtain the intraocular distance T by multiplying the distance Q by the average value of the refractive indexes of the media (cornea, lens, aqueous humor, vitreous body, etc.).

For example, the storage unit 202 stores, in advance, a schematic eye data (optical parameters) such as shape information or refractive index information indicating the structure of the eyeball in schematic eye of Gullstrand or schematic eye such as Sanz & Navarro. The intraocular distance calculator can calculate the intraocular distance using the schematic eye data stored in the storage unit 202. For example, the intraocular distance calculator obtains the intraocular distance T by multiplying the distance Q by the refractive index (for example, 1.375) of the schematic eye data.

The image correcting unit according to the first modification example corrects the tomographic image based on the intraocular distance T obtained as described above. That is, the image correcting unit corrects the tomographic image using one or more optical parameters corresponding to a passage site of the measurement light in the subject's eye E.

Second Modification Example

The image correcting processing performed by the image correcting unit 232 is not limited to the processing shown in FIG. 8.

Figure 10A:
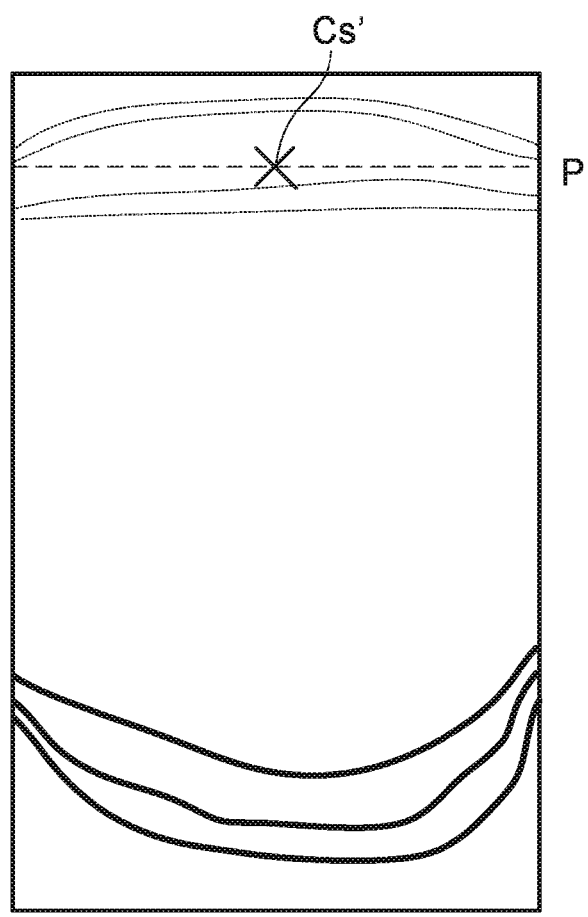
FIG. 10A is a schematic diagram for explaining the operation of the ophthalmologic apparatus according to a modification example of the embodiments.
Figure 10B:
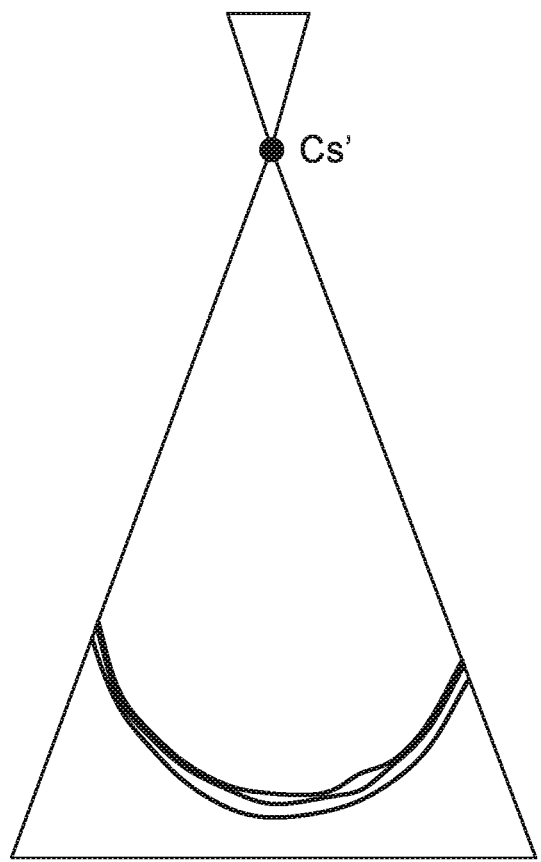
FIG. 10B is a schematic diagram for explaining the operation of the ophthalmologic apparatus according to a modification example of the embodiments.

FIGS. 10A and 10B show diagrams explaining the operation of the image correction unit according to the second modification example of the embodiments. FIG. 10A shows a diagram explaining the specifying processing of the scan center position performed by the intraocular distance calculator according to the second modification example. FIG. 10B shows diagrams explaining the image correction processing performed by the image correction unit according to the second modification example.

In the same manner as the first modification example, the intraocular distance calculator according to the second modification example obtains a variance value for each line in the B scan direction and specifies a line having a luminance value equal to or larger than a threshold and having a minimum variance value as the pupil position(s) P, for the tomographic image acquired in step S14. The intraocular distance calculator specifies the scan center position Cs' in the pupil position P. For example, the intraocular distance calculator specifies a center position in the B scan direction in the pupil position P, as the scan center position Cs'. Alternatively, the intraocular distance calculator may specify the scan center position Cs' using the schematic eye data, assuming that the eyeball optical system of the subject's eye E is similar to that of the schematic eye. Alternatively, the intraocular distance calculator may specify the scan center position Cs' by performing known ray tracing processing.

The image correcting unit according to the second modification example corrects each of a plurality of A scan images based on the intraocular distance corresponding to the each of the plurality of A scan images, shown in FIG. 10B. The image correcting unit generates the corrected image in which each of the corrected tomographic images is arranged along a direction passing through the scan center position Cs' and corresponding to the traveling direction of the measurement light. Specifically, the image correcting unit corrects each of a first tomographic image and a second tomographic image based on the intraocular distance, the first tomographic image being formed using the measurement light in a first traveling direction, the second tomographic image being formed using the measurement light in a second direction. The image correcting unit generates the corrected image in which the corrected first tomographic image is arranged along a direction passing through the scan center position Cs' and corresponding to the first traveling direction and the corrected second tomographic image is arranged along a direction passing through the scan center position Cs' and corresponding to the second traveling direction.

Thereby, the corrected tomographic images are arranged around the scan center position Cs'. Therefore, the corrected image reflecting the actual eyeball structure of the subject's eye E can be acquired.

Third Modification Example

As described above, the control unit 200 can change a depth range in the traveling direction of the measurement light, by changing the sweep frequency of the wavelength in the wavelength swept light source. For example, in the third modification example, a tomographic image in a long depth range is corrected based on the intraocular distance accurately obtained using a tomographic image in a short depth range with high accuracy.

Figure 11:
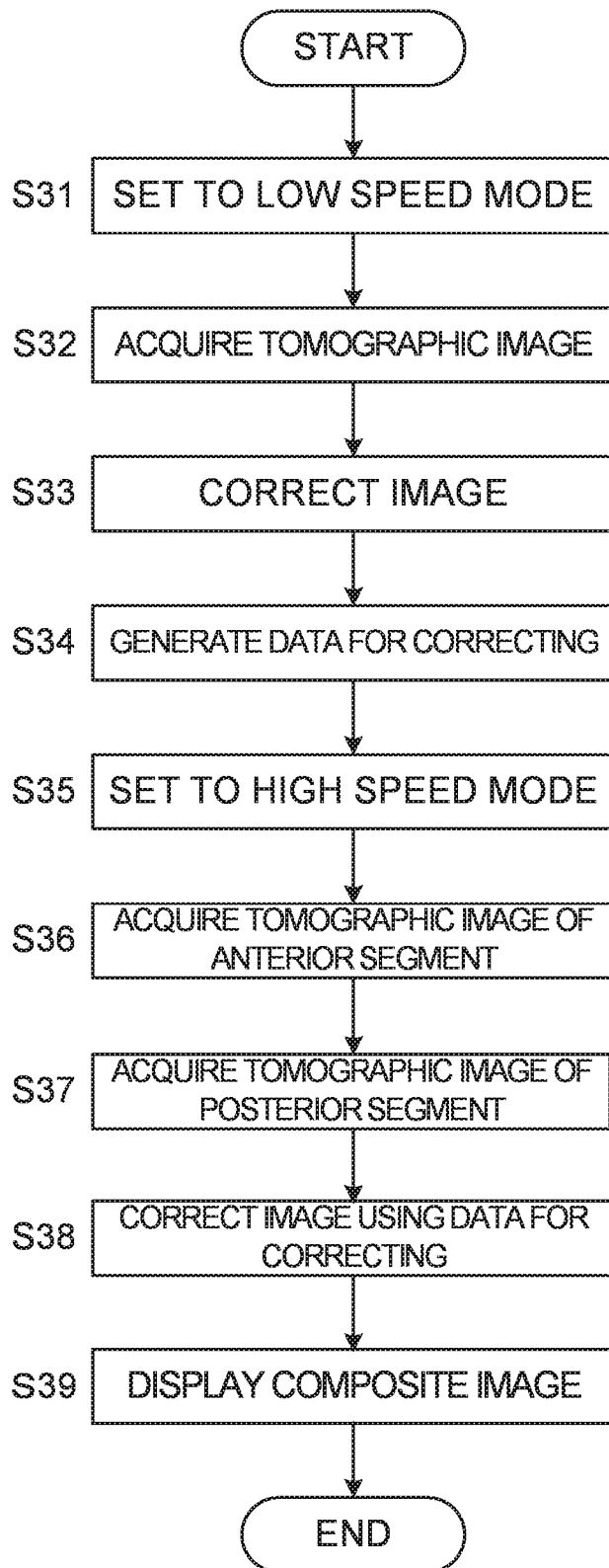
FIG. 11 is a flow chart illustrating an example of the operation of the ophthalmologic apparatus according to a modification example of the embodiments.

FIG. 11 shows an outline of an example of the operation of the ophthalmologic apparatus according to the third modification example of the embodiments. FIG. 11 shows a flow chart of the example of the operation of the ophthalmologic apparatus according to the third modification example. The storage unit 202 in the control unit 200 stores computer programs for realizing the processing shown in FIG. 11. The controller 201 in the control unit 200 operates according to the computer programs, and thereby the controller 201 performs processing shown in FIG. 11. In FIG. 11, it is assumed that the alignment is completed in advance.

(S31: Set to Low Speed Mode)

First, the control unit 200 sets the operation mode of the OCT light source to the low speed mode. Thereby, the OCT light source emits the output light whose output wavelength changes at the sweep frequency of the wavelength corresponding to the low speed mode.

(S32: Acquire Tomographic Image)

Next, the control unit 200 performs OCT using the interference optical system 40, and causes the image forming unit 220 to form a tomographic image of the subject's eye E.

(S33: Correct Image)

Subsequently, the control unit 200 controls the intraocular distance calculator to calculate the intraocular distance from the tomographic image formed in step S32, and controls the image correcting unit to generate the corrected image based on the calculated intraocular distance. The image correcting unit generates the corrected image as shown in FIG. 10B, for example.

(S34: Generate Data for Correcting)

The control unit 200 controls the data processing unit 230 to generate data for correcting from the corrected image generated in step S33. For example, the data processing unit 230 generates the data for correcting including the shape information (for example, curvature or intraocular distance) of a predetermined site such as a cornea or a retina, by analyzing the corrected image generated in step S33.

(S35: Set to High Speed Mode)

Next, the control unit 200 sets the operation mode of the OCT light source to the high speed mode. Thereby, the OCT light source emits the output light whose output wavelength changes at the sweep frequency of the wavelength corresponding to the high speed mode. The sweep frequency of the wavelength in step S35 is higher than the sweep frequency of the wavelength in step S31.

(S36: Acquire Tomographic Image of Anterior Segment)

Subsequently, the control unit 200 performs OCT using the interference optical system 40 on the anterior segment of the subject's eye E, by changing the wavelength sweep range of the OCT light source, for example. The control unit 200 causes the image forming unit 220 to form a tomographic image of the anterior segment of the subject's eye E, using the interference data obtained by the interference optical system 40.

(S37: Acquire Tomographic Image of Posterior Segment)

In the same manner, the control unit 200 performs OCT using the interference optical system 40 on the posterior segment of the subject's eye E, by changing the wavelength sweep range of the OCT light source, for example. The control unit 200 causes the image forming unit 220 to form a tomographic image of the posterior segment of the subject's eye E, using the interference data obtained by the interference optical system 40.

(S38: Correct Image Using Data for Correcting)

The control unit 200 controls the image correcting unit to correct the tomographic image of the anterior segment acquired in step S36, based on the data for correcting generated in step S34, and to generate a corrected image of the anterior segment. The image correcting unit corrects the tomographic image of the anterior segment so as to change the shape of the predetermined site according to the curvature obtained in step S34. Further, the image correcting unit corrects the tomographic image of the anterior segment based on the intraocular distance obtained in step S34. In the same manner, the control unit 200 controls the image correcting unit to correct the tomographic image of the posterior segment acquired in step S37, based on the data for correcting generated in step S34, and to generate a corrected image of the posterior segment.

(S39: Display Composite Image)

The control unit 200 causes the data processing unit 230 to generate a composite image. The data processing unit 230 generates the composite image by superimposing at least one of the corrected image of the anterior segment and the corrected image of the posterior segment on the corrected image generated in step S33. The corrected image of the anterior segment is generated in step S36. The corrected image of the posterior segment is generated in step S37. This terminates the operation of the ophthalmologic apparatus according to the third modification example (END).

As described above, in the third modification example, the image forming unit 220 is configured to form the tomographic image (a third tomographic image) of the subject's eye E in the first depth range in the traveling direction of the measurement light and the tomographic image (a fourth tomographic image) of the subject's eye E in the second depth range including the first depth range, the second depth range being longer than the first depth range, The tomographic image in the first depth range is a higher definition image than the tomographic image in the second depth range. For example, the data processing unit 230 generates the data for correcting by analyzing the tomographic image in the first depth range. The data for correcting may be the intraocular distance obtained by analyzing the tomographic image in the first depth range. The image correcting unit corrects the tomographic image in the second depth range based on the data for correcting (for example, intraocular distance).

Thereby, the tomographic image with a long depth range and low image quality can be corrected using the data for correcting obtained from a high-definition tomographic image with a short depth range. Therefore, the correction with high accuracy can be performed on the tomographic image with low image quality.

Fourth Modification Example

In the embodiments or the modification examples thereof, the case has been described in which the angle of view is changed by changing the deflection angle of the measurement light using the optical scanner 30. However, the configuration of the ophthalmologic apparatus according to the embodiments is not limited thereto.

For example, the ophthalmologic apparatus may change the angle of view by switching objective lenses having different refractive powers. Even in this case, the image correcting unit can correct the tomographic image according to the angle of view changed by switching the refracting power of the objective lens as in the embodiments or modification examples of thereof described above.

When a first angle of view is set using a predetermined objective lens, the control unit 200 causes the optical scanner 30 to scan the subject's eye E with the measurement light, and causes the image forming unit 220 to form a first image representing a first range of the subject's eye. Further, the control unit 200 causes the image correcting unit to correct the first image based on the intraocular distance as described above, and causes the corrected first image to be displayed on the display of the display unit 250. On the other hand, when a second angle of view narrow than the first angle of view is set by switching objective lens, the control unit 200 causes the optical scanner 30 to scan the subject's eye E with the measurement light, and causes the image forming unit 220 to form a second image representing a second range of the subject's eye E. Further, the control unit 200 causes the formed second image to be displayed on the display of the display unit 250.

That is, since the image quality deteriorates as the angle of view becomes wider, the tomographic image acquired at the wider angle of view is corrected in the same manner as in the embodiments or modification examples described above, and the tomographic image acquired at the narrower angle of view is not performed the correction described above.

Alternatively, for example, the ophthalmologic apparatus may change the angle of view by rotating the apparatus optical system around the pupil of the subject's eye E. Even in this case, the image correcting unit can correct the tomographic image according to the angle of view changed by rotating the apparatus optical system as in the embodiments or modification examples of thereof described above.

<Actions and Effects>

The effects of the ophthalmologic apparatus according to the embodiments are explained.

A ophthalmologic apparatus (1) according to some embodiments includes an optical scanner (30), an interference optical system (40), an image forming unit (image forming unit 220), an intraocular distance calculator (231), an image correcting unit (232), and a controller (control unit 200, controller 201). The optical scanner is disposed at an optically substantially conjugate position with a first site (scan center position, center of the pupil) of a subject's eye. The interference optical system is configured to split light from a light source (OCT light source) into reference light and measurement light, to project the measurement light onto the subject's eye via the optical scanner, and to detect interference light between returning light of the measurement light from the subject's eye and the reference light via the optical scanner. The image forming unit is configured to form a tomographic image of the subject's eye corresponding a first traveling direction of the measurement light deflected by the optical scanner, based on a detection result of the interference light obtained by the interference optical system. The intraocular distance calculator is configured to obtain an intraocular distance between predetermined sites of the subject's eye based on the detection result of the interference light. The image correcting unit is configured to correct the tomographic image formed by the image forming unit, based on the intraocular distance obtained by the intraocular distance calculator. The controller is configured to control at least the optical scanner.

According to such a configuration, the intraocular distance is obtained from the tomographic image acquired using the interference optical system, and the tomographic image is corrected based on the obtained intraocular distance. Thereby, even when the deflection angle of the measurement light is large, the distortion of the tomographic image of the subject's eye can be corrected with high accuracy.

In the ophthalmologic apparatus according to some embodiments, the image forming unit is configured to form a plurality of tomographic images corresponding to a plurality of traveling directions of the measurement light deflected by the optical scanner. The image correcting unit is configured to correct each of the plurality of tomographic images formed by the image forming unit based on the intraocular distance, and to generate a corrected image in which the corrected plurality of tomographic images is arranged along a direction corresponding to an optical axis direction of the interference optical system.

According to such a configuration, a plurality of tomographic images according to a plurality of traveling directions of the measurement light is formed, each of the formed plurality of tomographic images is corrected based on the intraocular distance, and the corrected image in which the corrected plurality of tomographic images is arranged along direction corresponding to the optical axis of the interference optical system is generated. Thereby, the corrected image in which the aberration of the eyeball optical system of the subject's eye is compensated can be easily acquired.

In the ophthalmologic apparatus according to some embodiments, the image correcting unit is configured to correct each of the plurality of tomographic images so that the distance between the predetermined sites in each of the tomographic images becomes a constant value.

According to such a configuration, the corrected image having a flat tomographic structure in which the intraocular distance in a plurality of tomographic images is constant can be acquired.

In the ophthalmologic apparatus according to some embodiments, the image forming unit is configured to form a first tomographic image of the subject's eye and a second tomographic image of the subject's eye, the first tomographic image corresponding to the first traveling direction, the second tomographic image corresponding to a second traveling direction of the measurement light deflected by the optical scanner. The image correcting unit is configured to correct each of the first tomographic image and the second tomographic image based on the intraocular distance, and to generate a corrected image in which the corrected first tomographic image is arranged along a direction passing through the first site and corresponding to the first traveling direction and the corrected second tomographic image is arranged along a direction passing through the first sited and corresponding to the second traveling direction.

According to such a configuration, the corrected image in which the tomographic images are arranged along the traveling direction of the measurement light passing through the first site is generated. Thereby, the corrected image reflecting an actual structure of the subject's eye can be acquired.

In the ophthalmologic apparatus according to some embodiments, the image forming unit is configured to form a third tomographic image of the subject's eye in a first depth range in a traveling direction of the measurement light and a fourth tomographic image of the subject's eye in a second depth range including the first depth range, the second depth range being longer than the first depth range. The intraocular distance calculator is configured to obtain the intraocular distance based on the third tomographic image. The image correcting unit is configured to correct the fourth tomographic image based on the intraocular distance.

According to such a configuration, the tomographic image with low image quality is corrected based on the intraocular distance obtained from the tomographic image with high image quality. Thereby, the tomographic image with low image quality can be corrected with high accuracy.

In the ophthalmologic apparatus according to some embodiments, the light source is a wavelength swept light source that can change a sweep frequency of a wavelength. The controller is configured to cause the image forming unit to form a plurality of tomographic images having different depth ranges by changing the sweep frequency.

According to such a configuration, even when the deflection angle of the measurement light is large, the distortion of the tomographic image of an arbitrary site of the subject's eye can be corrected with high accuracy.

The ophthalmologic apparatus according to some embodiments includes an angle-of-view change unit (optical scanner 30) configured to change an angle of view. The image correcting unit is configured to correct the tomographic image according to the angle of view changed by the angle-of-view change unit.

According to such a configuration, the tomographic image can be corrected according to the scan length that differs depending on the deflection angle of the measurement light. Therefore, the tomographic image can be corrected according to the aberrations of the eyeball optical system of the subject's eye. Thereby, the distortion of the tomographic image according to the subject's eye can be corrected with high accuracy.

In the ophthalmologic apparatus according to some embodiments, when a first angle of view is set by the angle-of-view change unit, the controller is configured to cause the optical scanner to scan the subject's eye with the measurement light, to cause the image forming unit to form a first image representing a first range of the subject's eye, to cause the image correcting unit to correct the first image based on the intraocular distance, and to cause the corrected first image to be displayed on a display means (display of the display unit 250). When a second angle of view narrower than the first angle of view is set by the angle-of-view change unit, the controller is configured to cause the optical scanner to scan the subject's eye with the measurement light, to cause the image forming unit to form a second image representing a second range of the subject's eye, and to cause the formed second image to be displayed on the display means.

According to such a configuration, the tomographic image is corrected merely when the angle of view is wide, and the high-definition tomographic images with a narrow angle of view is not corrected. Thereby, merely a tomographic image having a wide angle of view and low image quality can be corrected with high accuracy.

The ophthalmologic apparatus according to some embodiments includes a storage unit (202) configured to store one or more optical parameters corresponding to passage sites of the measurement light in the subject's eye. The image correcting unit is configured to correct the tomographic image using the one or more optical parameters.

According to such a configuration, the tomographic image can be corrected with high accuracy corresponding to the passage site of the measurement light.

In the ophthalmologic apparatus according to some embodiments, the intraocular distance calculator is configured to obtain an intraocular distance between the predetermined sites, for each A scan. The image correcting unit is configured to correct the tomographic image based on the intraocular distance obtained by the intraocular distance calculator, for each A scan.

According to such a configuration, the tomographic image is corrected for each A scan. Thereby, even when the deflection angle of the measurement light is large, the distortion of the tomographic image of the subject's eye can be corrected with high accuracy.

In the ophthalmologic apparatus according to some embodiments, the intraocular distance calculator is configured to obtain an intraocular distance between the predetermined sites, in units of a plurality of A scans. The image correcting unit is configured to correct the tomographic image based on the intraocular distance obtained the intraocular distance calculator, in units of the plurality of A scans.

According to such a configuration, the tomographic image is corrected in units of the plurality of A scans. Thereby, even when the deflection angle of the measurement light is large, the distortion of the tomographic image of the subject's eye can be corrected with high accuracy.

In the ophthalmologic apparatus according to some embodiments, the intraocular distance is axis length.

According to such a configuration, even when the deflection angle of the measurement light is large, the distortion of the tomographic image of the subject's eye can be corrected with high accuracy according to the axial length.

In the ophthalmologic apparatus according to some embodiments, the intraocular distance is a distance from the first site to a retina.

According to such a configuration, even when the deflection angle of the measurement light is large, the distortion of the tomographic image of the subject's eye can be corrected with high accuracy according to the distance from the first site to the retina.

A ophthalmologic information processing apparatus includes an image forming unit (image forming unit 220), an intraocular distance calculator (231), and an image correcting unit (232). The image forming unit is configured to form a tomographic image of a subject's eye based on data (interference data) acquired using optical coherence tomography, the optical coherence tomography using an optical scanner (30) disposed at an optically substantially conjugate position with a first site (scan center position, center of the pupil) of the subject's eye (E). The intraocular distance calculator is configured to obtain an intraocular distance between predetermined sites of the subject's eye based on the data. The image correcting unit is configured to correct the tomographic image formed by the image forming unit, based on the intraocular distance obtained by the intraocular distance calculator.

In the ophthalmologic information apparatus according to some embodiments, the image forming unit is configured to form a plurality of tomographic images corresponding to a plurality of traveling directions of the measurement light deflected by the optical scanner. The image correcting unit is configured to correct each of the plurality of tomographic images formed by the image forming unit based on the intraocular distance, and to generate a corrected image in which the corrected plurality of tomographic images is arranged along directions corresponding to traveling directions of the measurement light.

In the ophthalmologic information processing apparatus according to some embodiments, the image correcting unit is configured to correct each of the plurality of tomographic images so that the distance between the predetermined sites in each of the tomographic images becomes a constant value.

In the ophthalmologic information processing apparatus according to some embodiments, the image forming unit is configured to form a first tomographic image of the subject's eye and a second tomographic image of the subject's eye, the first tomographic image corresponding to a first traveling direction of the measurement light, the second tomographic image corresponding to a second traveling direction of the measurement light deflected by the optical scanner. The image correcting unit is configured to correct each of the first tomographic image and the second tomographic image based on the intraocular distance, and to generate a corrected image in which the corrected first tomographic image is arranged along a direction passing through the first site and corresponding to the first traveling direction and the corrected second tomographic image is arranged along a direction passing through the first sited and corresponding to the second traveling direction.

An ophthalmologic information processing method according to some embodiments is implemented by the ophthalmologic information processing apparatus according to the embodiments described above. A program for realizing the ophthalmologic information processing method according to some embodiments can be stored in any kind of computer non-transitory recording medium. The recording medium may be an electronic medium using magnetism, light, magneto-optical, semiconductor, or the like. Typically, the recording medium is a magnetic tape, a magnetic disk, an optical disk, a magneto-optical disk, a flash memory, a solid state drive, or the like.

The above-described embodiments are merely examples for carrying out the present invention. Those who intend to implement the present invention can apply any modification, omission, addition, or the like within the scope of the gist of the present invention.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus, comprising:
   an optical scanner disposed at a position with respect to a first site of a subject's eye;
   an interference optical system configured to split light from a light source into reference light and measurement light, to project the measurement light onto the subject's eye via the optical scanner, and to detect interference light between returning light of the measurement light from the subject's eye and the reference light via the optical scanner;
   an image forming circuit configured to form a tomographic image of the subject's eye corresponding a first traveling direction of the measurement light deflected by the optical scanner, based on a detection result of the interference light obtained by the interference optical system;
   an intraocular distance calculator circuit configured to obtain an intraocular distance between predetermined sites of the subject's eye based on the detection result of the interference light;
   an image correcting circuit configured to correct the tomographic image formed by the image forming circuit, based on the intraocular distance obtained by the intraocular distance calculator circuit; and
   a controller circuit configured to control at least the optical scanner, wherein
   the image forming circuit is configured to form a plurality of tomographic images corresponding to a plurality of traveling directions of the measurement light deflected by the optical scanner,
   the image correcting circuit is configured to correct each of the plurality of tomographic it aces formed by the image forming circuit based on the intraocular distance, and to generate a corrected image in which the corrected plurality of tomographic images is arranged along a direction corresponding to an optical axis direction of the interference optical system, and
   the image correcting circuit is configured to correct each of the plurality of tomographic images so that the distance between the predetermined sites in each of the tomographic images becomes a constant value.

2. The ophthalmologic apparatus of claim 1, wherein
   the intraocular distance calculator circuit is configured to obtain an intraocular distance between the predetermined sites, for each A scan, and
   the image correcting circuit is configured to correct the tomographic image based on the intraocular distance obtained by the intraocular distance calculator circuit, for each A scan.

3. The ophthalmologic apparatus of claim 1, wherein
   the intraocular distance calculator circuit is configured to obtain an intraocular distance between the predetermined sites, in units of a plurality of A scans, and
   the image correcting circuit is configured to correct the tomographic image based on the intraocular distance obtained the intraocular distance calculator circuit, in units of the plurality of A scans.

4. The ophthalmologic apparatus of claim 1, wherein
   the intraocular distance is axis length.

5. The ophthalmologic apparatus of claim 1, wherein
   the intraocular distance is a distance from the first site to a retina.

6. The ophthalmologic apparatus of claim 1, wherein the optical scanner is disposed at the position that is optically conjugate with the first site of the subject's eye.

7. An ophthalmologic apparatus, comprising:
   an optical scanner disposed at a position with respect to a first site of a subject's eye;
   an interference optical system configured to split light from a light source into reference light and measurement light, to project the measurement light onto the subject's eye via the optical scanner, and to detect interference light between returning light of the measurement light from the subject's eye and the reference light via the optical scanner;
   an image forming circuit configured to form a tomographic image of the subject's eye corresponding a first traveling direction of the measurement light deflected by the optical scanner, based on a detection result of the interference light obtained by the interference optical system;
   an intraocular distance calculator circuit configured to obtain an intraocular distance between predetermined sites of the subject's eye based on the detection result of the interference light;
   an image correcting circuit configured to correct the tomographic image formed by the image forming circuit, based on the intraocular distance obtained by the intraocular distance calculator circuit; and
   a controller circuit configured to control at least the optical scanner, wherein
   the image forming circuit is configured to form a first tomographic image of the subject's eye and a second tomographic image of the subject's eye, the first tomographic image corresponding to the first traveling direction, the second tomographic image corresponding to a second traveling direction of the measurement light deflected by the optical scanner, and the image correcting circuit is configured to correct each of the first tomographic image and the second tomographic image based on the intraocular distance, and to generate a corrected image in which the corrected first tomographic image is arranged along a direction passing through the first site and corresponding to the first traveling direction and the corrected second tomographic image is arranged along a direction passing through the first site and corresponding to the second traveling direction.

8. The ophthalmologic apparatus of claim 7, wherein
the intraocular distance calculator circuit is configured to obtain an intraocular distance between the predetermined sites, for each A scan, and
the image correcting circuit is configured to correct the tomographic image based on the intraocular distance obtained by the intraocular distance calculator circuit, for each A scan.

9. The ophthalmologic apparatus of claim 7, wherein
the intraocular distance calculator circuit is configured to obtain an intraocular distance between the predetermined sites, in units of a plurality of A scans, and
the image correcting circuit is configured to correct the tomographic image based on the intraocular distance obtained the intraocular distance calculator circuit, in units of the plurality of A scans.

10. The ophthalmologic apparatus of claim 7, wherein the intraocular distance is axis length.

11. The ophthalmologic apparatus of claim 7, wherein the intraocular distance is a distance from the first site to a retina.

12. The ophthalmologic apparatus of claim 7, wherein the optical scanner is disposed at the position that is optically conjugate with the first site of the subject's eye.

13. An ophthalmologic apparatus, comprising:
an optical scanner disposed at a position with respect to a first site of a subject's eye;
an interference optical system configured to split light from a light source into reference light and measurement light, to project the measurement light onto the subject's eye via the optical scanner, and to detect interference light between returning light of the measurement light from the subject's eye and the reference light via the optical scanner;
an image forming circuit configured to form a tomographic image of the subject's eye corresponding a first traveling direction of the measurement light deflected by the optical scanner, based on a detection result of the interference light obtained by the interference optical system;
an intraocular distance calculator circuit configured to obtain an intraocular distance between predetermined sites of the subject's eye based on the detection result of the interference light;
an image correcting circuit configured to correct the tomographic image formed by the image forming circuit based on the intraocular distance obtained by the intraocular distance calculator circuit; and
a controller circuit configured to control at least the optical scanner, wherein
the image forming circuit is configured to form a third tomographic image of the subject's eye in a first depth range in a traveling direction of the measurement light and a fourth tomographic image of the subject's eye in a second depth range including the first depth range, the second depth range being longer than the first depth range,
the intraocular distance calculator circuit is configured to obtain the intraocular distance based on the third tomographic image, and
the image correcting circuit is configured to correct the fourth tomographic image based on the intraocular distance.

14. The ophthalmologic apparatus of claim 13, wherein
the light source is a wavelength swept light source that can change a sweep frequency of a wavelength, and
the controller circuit is configured to cause the image forming circuit to form a plurality of tomographic images having different depth ranges by changing the sweep frequency.

15. The ophthalmologic apparatus of claim 13, wherein
the intraocular distance calculator circuit is configured to obtain an intraocular distance between the predetermined sites, for each A scan, and
the image correcting circuit is configured to correct the tomographic image based on the intraocular distance obtained by the intraocular distance calculator circuit, for each A scan.

16. The ophthalmologic apparatus of claim 13, wherein
the intraocular distance calculator circuit is configured to obtain an intraocular distance between the predetermined sites, in units of a plurality of A scans, and
the image correcting circuit is configured to correct the tomographic image based on the intraocular distance obtained the intraocular distance calculator circuit, in units of the plurality of A scans.

17. The ophthalmologic apparatus of claim 13, wherein the intraocular distance is axis length.

18. The ophthalmologic apparatus of claim 13, wherein the intraocular distance is a distance from the first site to a retina.

19. The ophthalmologic apparatus of claim 13, wherein the optical scanner is disposed at the position that is optically conjugate with the first site of the subject's eye.

20. An ophthalmologic apparatus comprising:
an optical scanner disposed at position with respect to a first site of a subject's eye;
an interference optical system configured to split light from a light source into reference light and measurement light, to project the measurement light onto the subject's eye via the optical scanner, and to detect interference light between returning light of the measurement light from the subject's eye and the reference light via the optical scanner;
an image forming circuit configured to form a tomographic image of the subject's eye corresponding a first traveling direction of the measurement light deflected by the optical scanner, based on a detection result of the interference light obtained by the interference optical system;
an intraocular distance calculator circuit configured to obtain an intraocular distance between predetermined sites of the subject's eye based on the detection result of the interference light;
an image correcting circuit configured to correct the tomographic image formed by the image forming circuit based on the intraocular distance obtained by the intraocular distance calculator circuit;

a controller circuit configured to control at least the optical scanner; and an angle-of-view change circuit configured to change are angle of view, wherein the image correcting circuit is configured to correct the tomographic image according to the angle of view changed by the angle-of-view change circuit, when a first angle of view is set by the angle-of-view change circuit, the controller circuit is configured to cause the optical scanner to scan the subject's eye with the measurement light, to cause the image forming circuit to form a first image representing a first range of the subject's eye, to cause the image correcting circuit to correct the first image based on the intraocular distance, and to cause the corrected first image to be displayed on a display, and when a second angle of view narrower than the first angle of view is set by the angle-of-view change circuit, the controller circuit is configured to cause the optical scanner to scan the subject's eye with the measurement light, to cause the image forming circuit to form a second image representing a second range of the subject's eye, and to cause the formed second image to the displayed on the display.

21. The ophthalmologic apparatus of claim 20, wherein
the intraocular distance calculator circuit is configured to obtain an intraocular distance between the predetermined sites, for each A scan, and
the image correcting circuit is configured to correct the tomographic image based on the intraocular distance obtained by the intraocular distance calculator circuit, for each A scan.

22. The ophthalmologic apparatus of claim 20, wherein
the intraocular distance calculator circuit is configured to obtain an intraocular distance between the predetermined sites, in units of a plurality of A scans, and
the image correcting circuit is configured to correct the tomographic image based on the intraocular distance obtained the intraocular distance calculator circuit, in units of the plurality of A scans.

23. The ophthalmologic apparatus of claim 20, wherein the intraocular distance is axis length.

24. The ophthalmologic apparatus of claim 20, wherein the intraocular distance is a distance from the first site to a retina.

25. The ophthalmologic apparatus of claim 20, wherein the optical scanner is disposed at the position that is optically conjugate with the first site of the subject's eye.

* * * * *